United States Patent
Kalas et al.

(10) Patent No.: US 6,379,385 B1
(45) Date of Patent: Apr. 30, 2002

(54) IMPLANT OF BONE MATTER

(75) Inventors: Rolf-Dieter Kalas, Söhrewald; Karl Koschatzky, Erlangen; Manfred Krüger, Arnoldshain; Christoph Schöpf, Möhrendorf, all of (DE)

(73) Assignee: Tutogen Medical GmbH (DE)

( * ) Notice: Subject to any disclaimer, the term of this patent is extended or adjusted under 35 U.S.C. 154(b) by 0 days.

(21) Appl. No.: 09/478,820

(22) Filed: Jan. 6, 2000

(51) Int. Cl.$^7$ .................................. A61F 2/28
(52) U.S. Cl. .................. 623/17.11; 623/16.11
(58) Field of Search ............. 623/16.11, 17.11, 623/17.19, 23.51

(56) References Cited

U.S. PATENT DOCUMENTS

| | | | |
|---|---|---|---|
| 3,848,601 A | 11/1974 | Ma et al. | 128/305 |
| 3,849,805 A | 11/1974 | Leake et al. | 3/1 |
| 3,892,648 A | 7/1975 | Phillips et al. | 204/181 |
| 3,918,100 A | 11/1975 | Shaw et al. | 3/1.9 |
| 4,309,777 A | 1/1982 | Patil | 3/1.91 |
| 4,349,921 A | 9/1982 | Kuntz | 3/1 |
| 4,501,269 A | 2/1985 | Bagby | 128/92 G |
| 4,550,448 A | 11/1985 | Kenna | 623/16 |
| 4,553,273 A | 11/1985 | Wu | 623/18 |
| 4,654,464 A | 3/1987 | Mittelmeier et al. | 623/16 |
| 4,678,470 A | 7/1987 | Nashef et al. | 623/16 |
| 4,743,257 A | 5/1988 | Tormala et al. | 623/16 |
| 4,834,757 A | 5/1989 | Brantigan | 623/17 |
| 4,846,837 A | 7/1989 | Kurze et al. | 623/16 |
| 4,871,578 A | 10/1989 | Adam et al. | 427/2 |
| 4,878,914 A | 11/1989 | Miwa et al. | 623/16 |
| 4,950,296 A | 8/1990 | McIntyre | 623/16 |
| 4,969,913 A | 11/1990 | Ojima | 623/66 |
| 4,983,182 A | 1/1991 | Kijima et al. | 623/16 |
| 5,053,049 A | 10/1991 | Campbell | 623/16 |
| 5,055,104 A | 10/1991 | Ray | 606/61 |
| 5,061,286 A | 10/1991 | Lyle | 623/16 |
| 5,192,325 A | 3/1993 | Kijima et al. | 623/16 |
| 5,211,664 A | 5/1993 | Tepic et al. | 623/16 |
| 5,263,985 A | 11/1993 | Bao et al. | 623/16 |
| 5,298,254 A * | 3/1994 | Prewett | 623/16.11 |
| 5,306,304 A | 4/1994 | Gendler | 623/16 |
| 5,403,317 A | 4/1995 | Bonutti | 606/80 |
| 5,458,638 A | 10/1995 | Kuslich et al. | 623/17 |
| 5,464,440 A | 11/1995 | Johansson | 623/16 |
| 5,489,308 A | 2/1996 | Kuslich et al. | 623/17 |
| 5,507,813 A | 4/1996 | Dowd et al. | 623/16 |
| 5,531,791 A | 7/1996 | Wolfinbarger, Jr. | 623/16 |
| 5,549,699 A | 8/1996 | MacMahon et al. | 623/22 |
| 5,556,379 A | 9/1996 | Wolfinbarger | 604/49 |
| 5,585,116 A | 12/1996 | Boniface et al. | 424/549 |
| 5,725,813 A | 3/1998 | Nies | 264/15 |
| 5,728,159 A | 3/1998 | Stroever et al. | 623/16 |
| 5,749,916 A | 5/1998 | Richelsoph | 623/17 |
| 5,769,897 A | 6/1998 | Harle | 623/16 |
| 5,797,871 A | 8/1998 | Wolfinbarger, Jr. | 604/49 |
| 5,814,084 A | 9/1998 | Grivas et al. | 623/16 |
| 5,895,427 A | 4/1999 | Kuslich et al. | 623/17 |
| 5,899,939 A | 5/1999 | Boyce et al. | 623/16 |
| 5,980,252 A * | 11/1999 | Samchukov | 623/16.11 |
| 6,123,731 A * | 9/2000 | Boyce | 623/16.11 |
| 6,143,030 A * | 11/2000 | Schroder | 623/16.11 |
| 6,149,688 A * | 11/2000 | Brosnahan | 623/16.11 |
| 6,200,347 B1 * | 3/2001 | Anderson | 623/16.11 |

FOREIGN PATENT DOCUMENTS

DE 29 10 627 A1 9/1980

* cited by examiner

*Primary Examiner*—Michael J. Milano
(74) *Attorney, Agent, or Firm*—Gifford, Krass, Groh, Sprinkle; Anderson & Citkowski, P.C.

(57) ABSTRACT

A spinal column implant consists of a base body of spongeous bone matter into which at least one load-carrying support element is embedded.

21 Claims, 1 Drawing Sheet

IMPLANT OF BONE MATTER

Figure 1:
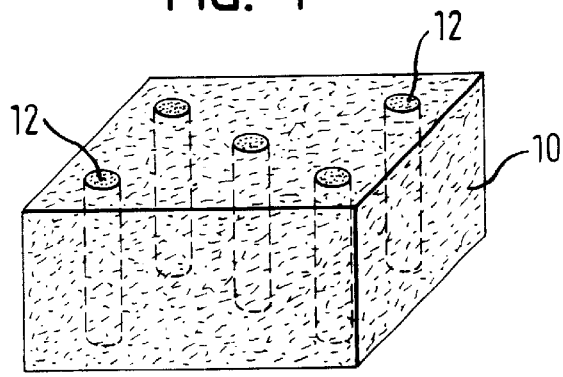

The present invention relates to an implant for the connection of bones and in particular to a spinal column implant for the fusion of vertebral bones which is introduced between two vertebral bones to be fused.

Through the degeneration of the vertebral disc, in particular of the vertebral disc nucleus (nucleus pulposus) a loss of height in the affected vertebral disc space often comes about which is connected with a loosening of the vertebral disc annulus (annulus fibrosus) and of the ligaments. Through this the spinal column becomes instable at this location. The result is a horizontal displaceability of the vertebral bodies relative to one another (spondylolisthesis), which leads to impairments of the nerve roots in this region and/or of the spinal cord together with the pain resulting from this.

The principle for treating these symptoms consists in the operative excavation of the vertebral disc nucleus and the laying in or insertion respectively of one—in the region of the cervical vertebral column—or of two—in the region of the lumbar vertebral column—sufficiently stable bodies in order to restore the normal height of the vertebral disc space. At the same time the horizontal displaceability must be prevented. This takes place either through the implant itself or through additional metal implants. These implants are subject in particular in the lumbar vertebral column to consideable forces, which can lead to the breakage of the metal implant. Therefore an attempt is made to have the intermediate vertebral insert grow together or fuse respectively as rapidly and as solidly as possible with the adjacent vertebral bodies.

A known possibility of fuhsing two vertebrae consists in the insertion of a suitably shaped cylinder or dowel into a prepared cavity which reaches the two vertebrae to be fused. The material which is required for this is removed beforehand from the patient for example from the pelvic ridge. From the thus won autogenic bone matter, that is, bone matter stemming from the same patient, an implant is produced and then inserted into the intervertebral space of the patient between the two vertebrae to be fused (autografting).

The object of the present invention therefore consists in creating an implant for the fusion of bones which restores the correct distance between the vertebral bodies and the stabilty of the spinal column, which provokes no immune reactions and which accelerates the healing process.

This object is satisfied by a spinal column implant with the features of claim 1.

A particular advantage of the spinal column implant in accordance with the invention is given through the material used, which, as a result of its biological origin does not represent a foreign body. Through this the implant, which is produced of bone matter, contributes in its entirety, that is, the support element of for example cortical bone matter as well as the base body of spongeous bone matter, to the fusion of the vertebral bodies in that it converts into the body's own tissue during the healing in.

Since the base body has no outer shell of hard bone matter, but rather consists of spongeous bone, the spongeous bone matter of the base body comes into direct contact with the bone surfaces of the vertebral bodies in order to form a bony connection with the latter and thereby to fuse them or to connect them to one another respectively.

The inventors have recognized that it is particularly advantageous to form the base body of spongeous, that is, relatively porous, bone matter in order to accelerate the healing in process. In order to be able however to take up the not inconsiderable forces which can arise between two vertebral bodies which are to be fused with one another, in accordance with the invention at least one load-carrying support element is embedded in the base body of spongeous bone matter which extends from one side to an oppositely lying side of the base body. The support element thus serves as a load-carrying part, in contrast to which the base body substantially has the function of seating the support element and enabling the growing together process with the surrounding bone matter.

In the description, the drawings and the subordinate claims, further advantageous embodiments of the spinal column implant in accordance with the present invention are set forth.

In accordance with a first advantageous embodiment the at least one support element consists of compact or of cortical bone respectively. Through this it is ensured on the one hand that high forces can be taken up by the spinal column implant. On the other hand the implant has no artifacts, which further accelerates the healing in process.

The support element can preferably be formed in the manner of a pin or a column respectively, with it also being possible for a plurality of support elements to be embedded in parallel into the base body. Depending on the stress distribution the support elements can also have different cross-sections in this situation.

In accordance with a further embodiment of the invention the support element is designed to be areal or wall-like, through which yet higher stresses on the implant are possible. In this it is advantageous when a plurality of areal support elements, the planes of which intersect, are embedded in the base body.

The support element or support elements can terminate at the outer contour of the base body or project beyond the outer contour of the base body in order to facilitate the fitting in of the implant between two vertebrae to be fused.

In accordance with a further embodiment of the invention the base body can contain at least one cavity which is accessible from its outer side for the reception of bone powder or bone granulate. The introduction of materials of this kind into a cavity of this kind improves the healing in process yet further.

In order to facilitate an integration of the base body between two vertebrae to be fused, the base body can furthermore have a surface which is corrugated, toothed or provided with knobs. Furthermore, the outer shape of the base body can also vary. The latter can be formed in the shape of a block, a rectangular parallelepiped or a wedge, with it being possible for rounded off corner contours or curved base bodies to be advantageous.

The implant is preferably matched in its size to the intervertebral space which is present between the adjacent vertebrae after the excavation of the intervertebral body. The application of the spinal column implant in accordance with the invention takes place after excavation of the vertebral disc with subsequent exposure of the vertebral bodies lying above and below it without it being necessary to damage healthy bone matter for this. This brings about the advantage that the existing intervertebral space is not enlarged and the supporting structures remain intact.

In accordance with the invention a suitable allogenic or xenogenic bone matter is processed in such a manner that it is preserved, is capable of storage and can be used in accordance with its purpose. The preservation of the bone matter can for example take place by means of freeze drying. The spongeous bone matter is preferably produced through solvent dehydration of native bone matter by means of an organic solvent which is miscible with water, e.g. methanol, ethanol, propanol, isopropanol, acetone, methyl ethyl ketone or mixtures of these solvents. The preservation and sterilization of the bone matter in accordance with this method is also a subject matter of the patent DE 29 06 650, the contents of which are taken up into the disclosure of the present application through this reference.

This method serves for the production of transplant preserves and enables a dehydration and exposure right into the fine structure of the fibrils of the bone matter, so that the processed bone matter has a morphological structure in a histological view which is very similar to that of the natural bone, and thus the desired properties of the bone matter are retained. This method of solvent dehydration also has the advantage that a substantially lower apparative cost and complexity is required in comparison with freeze drying.

Furthermore, the spongeous bone matter can also be produced through solvent dehydration of bone matter with the subsequent terminal sterilization, in particular through irradiation with gamma rays. Alternatively, the spongeous bone matter can be produced through aseptic processing of bone matter without terminal sterilization.

Figure 2:
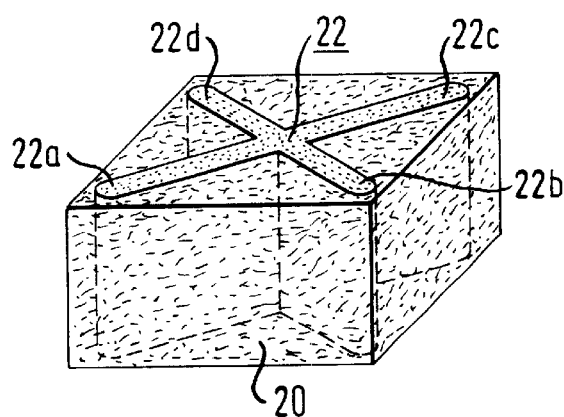
Figure 3:
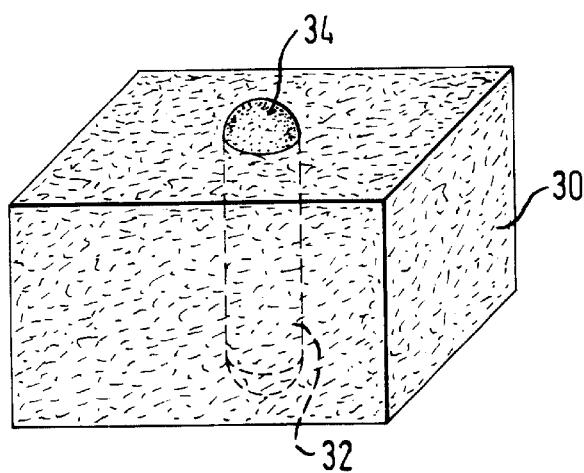

In the following the present invention will be described in a purely exemplary manner with reference to an exemplary embodiments of spinal column implant in accordance with the invention and with reference to the accompanying drawings. It shows:

FIG. 1 a schematic perspective view of a first embodiment of a spinal column implant in accordance with the present invention;

FIG. 2 a schematic perspective view of a further embodiment of a spinal column implant in accordance with the present invention; and FIG. 3 a schematic perspective view of a third embodiment of a spinal column implant in accordance with the present invention.

In the figures the same reference symbols designate in each case the same components of the illustrated embodiments. The illustrated exemplary embodiments are suitable both for the cervical and for the lumbar fusion of vertebral bones.

The exemplary embodiment of a spinal, column implant in accordance with the invention which is illustrated in FIG. 1 consists of a base body 10 of spongeous bone matter, which is designed to have substantially the shape of a rectangular parallelepiped. In the illustrated exemplary embodiment a plurality of, in the illustrated exemplary embodiment five, support elements 12 which consist of cortical bone are embedded into the base body 10. The support elements are formed as cylindrical pins and are embedded parallel spaced to one another into the base body 10. For this the base body 10 of spongeous bone matter is provided with corresponding parallel bores into which the support elements 12 are fitted in. The support elements 12 are substantially as long as the base body 10 is high, so that each support element 12 extends from one side of the base body to its oppositely lying side.

In the exemplary embodiment illustrated in FIG. 1 the end sides of the load-carrying support elements 12 substantially align with the outer contour of the base body 10.

FIG. 2 shows a further embodiment of a spinal column implant which consists of a base body 20 of spongeous bone matter which is designed having the shape of a rectangular parallelepiped. A load-carrying support element 22 which consists of four wall sections 22a, 22b, 22c and 22d and the planes of which intersect in the middle of the support element 22 is embedded into the base body 20. The support element 22 is milled in a single piece out of cortical bone and forms in plan view the shape of a diagonal cross. The base body 20 of spongeous bone matter is provided with a milling-out corresponding to the outer contour of the support element 22 so that the support element 22 of cortical bone can be inserted into this milling-out.

In this embodiment the end sides of the support element 22 again align with the outer contour of the base body 20, i.e. the lower side of the support element 22 aligns substantially with the lower side of the base body 20 and the upper side of the support element 22 aligns substantially with its upper side.

FIG. 3 shows a further embodiment of a spinal column implant which consists of a base body 30 of spongeous bone matter having the shape of a rectangular parallelepiped. Similarly as in the embodiment of FIG. 1 a pin-like support element 32 which consists of cortical bone is embedded in the center of the base body 30. As can be recognized, the end sides of the support element 32 are rounded off in the manner of a dome so that the support element 32 projects with its dome-shaped end side 34 beyond the outer contour of the base body 30. The opposite end side of the support element 32 is formed in the same way and likewise projects beyond the base body 30.

The securing of the support elements in the base body can take place through press seating or through adhesive bonding or another suitable securing means. Likewise, a large number of variations is possibly in the design of the support elements. Instead of the illustrated exemplary embodiments, merely a wall-like support element can be inserted. Pin-like and wall-like support elements can however also be combined with one another.

The base body of spongeous bone matter can have various other surface designs in addition to the illustrated rectangular parallelepipedal shape. For example its surface can be provided with knobs; it can be formed to be corrugated or toothed. The outer shape of the base body can be wedge-like, rounded off or also curved in the manner of a banana.

Furthermore, at least one cavity which is accessible from the outer side of the base body and which can be filled with bone powder or bone granulate can be provided in the base body In principle the size of the base body is matched to the predetermined location at which the implant is to be inserted. The outer dimensions of a spinal column implant of this kind can, depending on the location of use in cervical or lumbar application, for example be as follows: length 15 to 23 mm, width 8 to 13 mm, height 5 to 13 mm.

The edges of the base body can be rounded off in order to facilitate the introduction of the implant. Furthermore, at least one reception opening for an application tool can be provided.

The spongeous bone matter of the base body can be of human or animal, in particular bovine, origin and preferably has osteoinductive properties in order to favor the healing in process.

LIST OF REFERENCE SYMBOLS 10 base body
12 support element
20 base body
22 support element
22a–22d partial wall
30 base body
32 support element
34 end side

We claim:

1. Spinal column implant consisting of a base body (10, 20, 30) of spongeous bone matter into which at least one load-carrying support element (12, 22, 32) is entirely embedded therein.

2. Spinal column implant in accordance with claim 1, with the support element (12, 22, 32) extending from one side to an oppositely lying side of the base body (10, 20, 30).

3. Spinal column implant in accordance with claim 1, with the support element (12, 22, 32) consisting of compact or cortical bone.

4. Spinal, column implant in accordance with claim 1, with the support element being formed in the manner of a pin (12, 32).

5. Spinal column implant in accordance with claim 1, with a plurality of parallel support elements (12) being embedded into the base body.

6. Spinal column implant in accordance with claim 1, with the support element (22) being formed areally or in the manner of a wall.

7. Spinal column implant in accordance with claim 1, with a plurality of areal support elements (20a–20d), the planes of which intersect, being embedded into the base body (20).

8. Spinal column implant in accordance with claim 1, with the support element (32) projecting beyond the outer contour of the base body (30).

9. Spinal column implant in accordance with claim 1, with the base body containing at least one cavity for the reception of bone powder or bone granulate which is accessible from its outer side.

10. Spinal column implant in accordance with claim 1, with the base body having a surface which is corrugated, toothed or provided with knobs.

11. Spinal column implant in accordance with claim 1, with the base body being substantially block-shaped and with at least one through-going pin being embedded into this block as a support element (12, 32).

12. Spinal column implant comprising a unitary base body of spongeous bone matter into which at least one load-carrying support element is entirely embedded therein.

13. Spinal column implant in accordance with claim 12, with the support element extending from one side to an oppositely lying side of the base body.

14. Spinal column implant in accordance with claim 12, with the support element consisting of compact or cortical bone.

15. Spinal column implant in accordance with claim 12, with the support element being formed in the manner of a pin.

16. Spinal column implant in accordance with claim 12, with a plurality of parallel support elements being embedded into the base body.

17. Spinal column implant in accordance with claim 12, with the support element being formed areally or in the manner of a wall.

18. Spinal column implant in accordance with claim 12, with a plurality of areal support elements, the planes of which intersect, being embedded into the base body.

19. Spinal column implant in accordance with claim 12, with the base body containing at least one cavity for the reception of bone powder or bone granulate which is accessible from its outer side.

20. Spinal column implant in accordance with claim 12, with the base body having a surface which is corrugated, toothed or provided with knobs.

21. Spinal column implant in accordance with claim 12, with the base body being substantially block-shaped and with at least one through-going pin being embedded into this block as a support element.

* * * * *